(12) United States Patent
Minvielle (10) Patent No.: US 10,790,062 B2
(45) Date of Patent: Sep. 29, 2020

(54) SYSTEM FOR TRACKING AND OPTIMIZING HEALTH INDICES

(71) Applicant: Eugenio Minvielle, Rye, NY (US)

(72) Inventor: Eugenio Minvielle, Rye, NY (US)

( * ) Notice: Subject to any disclaimer, the term of this patent is extended or adjusted under 35 U.S.C. 154(b) by 496 days.

(21) Appl. No.: 14/508,913

(22) Filed: Oct. 7, 2014

(65) Prior Publication Data

US 2015/0100350 A1 Apr. 9, 2015

Related U.S. Application Data (60) Provisional application No. 61/888,451, filed on Oct. 8, 2013.

(51) Int. Cl.
  *G06K 19/06* (2006.01)
  *G16H 50/30* (2018.01)
  *G16H 10/60* (2018.01)

(52) U.S. Cl.
  CPC ............ *G16H 50/30* (2018.01); *G16H 10/60* (2018.01)

(58) Field of Classification Search
  CPC ........ G06Q 50/22; G06Q 50/24; G06Q 40/08; G06Q 10/10; G06Q 10/06; G06Q 30/02; G06F 19/322; G06F 17/30; G06F 19/30; G06F 19/32; G06F 19/321; G06F 19/324; G06F 19/325; G06F 19/326; G06F 19/328; G06F 19/34; G06F 19/3418; G06F 19/3456; G06F 19/3462; G06F 19/3468; G06F 19/3475; G06F 19/3481; G06F 19/36; G06F 16/28; G06F 16/284; A61N 1/08; G16H 10/00; G16H 10/20; G16H 10/40; G16H 10/60; G16H 10/65; G16H 15/00; G16H 20/00; G16H 20/10; G16H 20/13; G16H 20/17; G16H 20/30; G16H 20/40; G16H 20/60; G16H 20/70; G16H 20/90; G16H 30/00; G16H 30/20; G16H 30/40; G16H 40/00; G16H 40/20; G16H 40/40; G16H 40/60; G16H 40/63; G16H 40/67; G16H 50/00; G16H 50/20; G16H 50/30;

(Continued)

(56) References Cited

U.S. PATENT DOCUMENTS 4,225,410 A   9/1980 Pace
4,555,930 A   12/1985 Leach et al.

(Continued)

FOREIGN PATENT DOCUMENTS

DE  10 2005 040206 A1   2/2007
EP    1 117 055 A2      7/2001

(Continued)

OTHER PUBLICATIONS

Office Action in U.S. Appl. No. 13/485,850, dated Mar. 19, 2015.

(Continued)

*Primary Examiner* — Maroun P Kanaan
(74) *Attorney, Agent, or Firm* — DLA Piper LLP (US)

(57) ABSTRACT

A system and method for tracking and optimizing health indices is provided. In some embodiments the system provides for tracking and/or optimizing health indices of one or more individuals having a particular genetic profile and adaptively managing external factors the individual experiences so as to optimize a change in one or more health indices based on the individual's genetic profile.

11 Claims, 2 Drawing Sheets

(58) Field of Classification Search
CPC ........ G16H 50/50; G16H 50/70; G16H 50/80;
G16H 70/00; G16H 70/20; G16H 70/14;
G16H 70/60; G16H 80/00; G09B 19/0092
See application file for complete search history.

(56) References Cited

U.S. PATENT DOCUMENTS

| | | | |
|---|---|---|---|
| 4,644,154 A | 2/1987 | Brogardh et al. | |
| 4,650,766 A | 3/1987 | Harm et al. | |
| 4,674,320 A | 6/1987 | Hirschfeld | |
| D333,782 S | 3/1993 | van Berlo | |
| 5,250,789 A | 10/1993 | Johnsen | |
| 5,412,560 A | 5/1995 | Dennision | |
| 5,442,669 A | 8/1995 | Medin | |
| 5,478,900 A | 12/1995 | Amano et al. | |
| 5,478,989 A | 12/1995 | Shepley | |
| 5,478,990 A | 12/1995 | Montanari et al. | |
| 5,673,691 A | 10/1997 | Abrams et al. | |
| 5,697,177 A | 12/1997 | Ludlow et al. | |
| 5,804,803 A | 9/1998 | Cragun et al. | |
| 5,853,790 A | 12/1998 | Glancy | |
| 5,872,721 A | 2/1999 | Huston et al. | |
| 5,937,387 A * | 8/1999 | Summerell ......... G06F 19/3456 600/301 | |
| 5,954,640 A | 9/1999 | Szabo | |
| 6,012,415 A | 1/2000 | Linseth | |
| 6,119,531 A | 9/2000 | Wendte et al. | |
| 6,182,725 B1 | 2/2001 | Sorvik | |
| 6,211,789 B1 | 4/2001 | Oldham et al. | |
| 6,270,724 B1 | 8/2001 | Woodaman | |
| 6,276,264 B1 | 8/2001 | Dumm | |
| 6,310,964 B1 | 10/2001 | Mohan et al. | |
| 6,325,878 B1 | 12/2001 | Borgstrom | |
| 6,356,940 B1 | 3/2002 | Short | |
| 6,387,049 B1 | 5/2002 | Moore | |
| 6,444,233 B1 | 9/2002 | Arntzen et al. | |
| 6,483,434 B1 | 11/2002 | Umiker | |
| 6,491,217 B2 | 12/2002 | Catan | |
| 6,502,411 B2 | 1/2003 | Okamoto | |
| 6,512,919 B2 | 1/2003 | Ogasawara | |
| 6,513,532 B2 | 2/2003 | Mault et al. | |
| 6,538,215 B2 | 3/2003 | Montagnino et al. | |
| 6,549,818 B1 | 4/2003 | Ali | |
| 6,553,386 B1 | 4/2003 | Alabaster | |
| 6,554,182 B1 | 4/2003 | Magnusson et al. | |
| 6,556,963 B1 | 4/2003 | Tetzlaff | |
| 6,571,603 B1 | 6/2003 | Doleman et al. | |
| D478,773 S | 8/2003 | Palen | |
| 6,616,047 B2 | 9/2003 | Catan | |
| 6,631,333 B1 | 10/2003 | Lewis et al. | |
| 6,671,698 B2 | 12/2003 | Pickett et al. | |
| 6,676,014 B2 | 1/2004 | Catan | |
| 6,689,398 B2 | 2/2004 | Haridas et al. | |
| 6,691,135 B2 | 2/2004 | Pickett et al. | |
| 6,716,462 B2 | 4/2004 | Prosise et al. | |
| 6,773,926 B1 | 8/2004 | Freund et al. | |
| 6,789,021 B2 | 9/2004 | Rendahl et al. | |
| 6,844,197 B1 | 1/2005 | Doleman et al. | |
| 6,874,000 B2 | 3/2005 | Sholl et al. | |
| 6,888,458 B2 | 5/2005 | Carlson | |
| 6,953,342 B2 | 10/2005 | Bisogno | |
| 6,975,910 B1 | 12/2005 | Brown et al. | |
| 6,982,640 B2 | 1/2006 | Lindsay et al. | |
| 7,024,369 B1 | 4/2006 | Brown et al. | |
| 7,076,438 B1 | 7/2006 | Tobelmann et al. | |
| 7,085,777 B2 | 8/2006 | Beck et al. | |
| 7,090,638 B2 | 8/2006 | Vidgen | |
| 7,103,481 B2 | 9/2006 | Negri | |
| 7,151,447 B1 | 12/2006 | Willms et al. | |
| 7,152,040 B1 | 12/2006 | Hawthorne et al. | |
| D534,758 S | 1/2007 | Lee et al. | |
| D539,072 S | 3/2007 | Kawata et al. | |
| D539,595 S | 4/2007 | Okuda et al. | |
| D540,613 S | 4/2007 | Jeon | |
| D541,578 S | 5/2007 | Jeon | |
| 7,212,955 B2 | 5/2007 | Kirshenbau et al. | |
| 7,213,743 B2 | 5/2007 | Carlson et al. | |
| 7,215,420 B2 | 5/2007 | Gellerman et al. | |
| 7,237,400 B2 | 7/2007 | Owada | |
| 7,256,699 B2 | 8/2007 | Tethrake et al. | |
| 7,275,863 B1 | 10/2007 | Akers et al. | |
| 7,295,889 B2 | 11/2007 | Lahteenmaki | |
| D560,960 S | 2/2008 | Hillmann et al. | |
| 7,357,316 B2 | 4/2008 | Heckel et al. | |
| 7,359,802 B1 | 4/2008 | Lewis et al. | |
| 7,372,003 B2 | 5/2008 | Kates | |
| 7,396,550 B2 | 7/2008 | Angel | |
| 7,403,855 B2 | 7/2008 | Fuessley et al. | |
| 7,440,901 B1 | 10/2008 | Dlott et al. | |
| 7,474,965 B2 | 1/2009 | Johnson et al. | |
| 7,571,676 B2 | 8/2009 | Nelson et al. | |
| 7,620,531 B1 | 11/2009 | Johnson | |
| D607,264 S | 1/2010 | Lee | |
| 7,681,383 B2 | 3/2010 | Argetsinger et al. | |
| D618,488 S | 6/2010 | Knochner | |
| 7,743,591 B2 | 6/2010 | Meier et al. | |
| 7,797,204 B2 | 9/2010 | Balent | |
| 7,836,876 B2 | 11/2010 | Schellenberg | |
| 7,840,359 B2 | 11/2010 | Hsiung et al. | |
| 7,854,108 B2 | 12/2010 | Koselka et al. | |
| D633,326 S | 3/2011 | Shin et al. | |
| 7,951,079 B1 | 5/2011 | Moore | |
| 7,957,850 B2 | 6/2011 | Anderson | |
| 7,996,134 B2 | 8/2011 | Roberts | |
| 8,009,048 B2 | 8/2011 | Hyde et al. | |
| 8,033,237 B2 | 10/2011 | Havens et al. | |
| 8,082,809 B2 | 12/2011 | Luellen et al. | |
| D654,299 S | 2/2012 | Benold | |
| 8,112,303 B2 | 2/2012 | Eglen et al. | |
| D657,607 S | 4/2012 | Ohmae et al. | |
| 8,193,474 B2 | 6/2012 | Harris | |
| D665,220 S | 8/2012 | Ohmae et al. | |
| 8,285,593 B2 | 10/2012 | Bhatt et al. | |
| 8,314,701 B2 | 11/2012 | Grieco et al. | |
| D673,001 S | 12/2012 | Becze et al. | |
| 8,393,137 B1 | 3/2013 | Crosby | |
| 8,403,215 B2 | 3/2013 | Aihara et al. | |
| 8,490,862 B1 | 7/2013 | Minvielle | |
| 8,626,796 B2 | 1/2014 | McBride et al. | |
| 8,631,050 B1 | 1/2014 | Gayle | |
| D702,482 S | 4/2014 | Davis et al. | |
| 8,796,510 B2 | 8/2014 | Heard et al. | |
| 9,016,193 B2 | 4/2015 | Minvielle | |
| 2002/0004749 A1 | 1/2002 | Froseth et al. | |
| 2002/0011567 A1 | 1/2002 | Ozanich | |
| 2002/0040564 A1 | 4/2002 | Killingbeck et al. | |
| 2002/0059175 A1 | 5/2002 | Nakano | |
| 2002/0091593 A1 | 7/2002 | Fowler | |
| 2002/0106432 A1 | 8/2002 | Yamagata et al. | |
| 2002/0125313 A1 | 9/2002 | Broff | |
| 2002/0168456 A1 | 11/2002 | Robbins | |
| 2003/0006281 A1 | 1/2003 | Thomas et al. | |
| 2003/0027161 A1 | 2/2003 | Bejanin et al. | |
| 2003/0099157 A1 | 5/2003 | Quine | |
| 2003/0136960 A1 | 7/2003 | Goodman et al. | |
| 2003/0163354 A1 | 8/2003 | Shamoun | |
| 2003/0165602 A1 | 9/2003 | Garwood | |
| 2003/0185937 A1 | 10/2003 | Garwood | |
| 2003/0185948 A1 | 10/2003 | Garwood | |
| 2003/0227392 A1 | 12/2003 | Ebert et al. | |
| 2004/0045202 A1 | 3/2004 | Arrendale, III et al. | |
| 2004/0083201 A1 | 4/2004 | Sholl et al. | |
| 2004/0100380 A1 | 5/2004 | Lindsay et al. | |
| 2004/0130714 A1 | 7/2004 | Gellerman et al. | |
| 2004/0147038 A1 | 7/2004 | Lewis et al. | |
| 2004/0152131 A1 | 8/2004 | Hsieh | |
| 2004/0167724 A1 | 8/2004 | Federer et al. | |
| 2004/0191382 A1 | 9/2004 | Cooper et al. | |
| 2004/0201454 A1 | 10/2004 | Waterhouse et al. | |
| 2004/0215402 A1 | 10/2004 | Hsiung et al. | |
| 2004/0267098 A1 | 12/2004 | Moore | |
| 2005/0001728 A1 | 1/2005 | Appelt et al. | |
| 2005/0027726 A1 | 2/2005 | Guivarch et al. | |
| 2005/0049920 A1 | 3/2005 | Day et al. | |

(56) References Cited

U.S. PATENT DOCUMENTS

| | | |
|---|---|---|
| 2005/0075900 A1 | 4/2005 | Arguimbau, III |
| 2005/0079491 A1 | 4/2005 | Donne-Gousse et al. |
| 2005/0168325 A1 | 8/2005 | Lievre et al. |
| 2005/0171738 A1 | 8/2005 | Kadaba |
| 2005/0247213 A1 | 11/2005 | Slilaty |
| 2005/0248455 A1 | 11/2005 | Pope et al. |
| 2005/0251449 A1 | 11/2005 | Pape et al. |
| 2006/0015371 A1 | 1/2006 | Knauf et al. |
| 2006/0061454 A1 | 3/2006 | Debord et al. |
| 2006/0062835 A1 | 3/2006 | Weil |
| 2006/0073483 A1 | 4/2006 | White et al. |
| 2006/0078658 A1 | 4/2006 | Owens et al. |
| 2006/0099310 A1 | 5/2006 | Koekkoek |
| 2006/0130498 A1 | 6/2006 | Joshi et al. |
| 2006/0172048 A1 | 8/2006 | Etchells et al. |
| 2006/0178841 A1 | 8/2006 | Fernandez |
| 2006/0200480 A1 | 9/2006 | Harris et al. |
| 2006/0228428 A1 | 10/2006 | Kang et al. |
| 2006/0240174 A1 | 10/2006 | Jung et al. |
| 2006/0256132 A1 | 11/2006 | Shin et al. |
| 2006/0277064 A1 | 12/2006 | Cannata |
| 2006/0286211 A1 | 12/2006 | Lang |
| 2007/0016852 A1 | 1/2007 | Kim et al. |
| 2007/0036840 A1 | 2/2007 | Tuduri et al. |
| 2007/0055551 A1 | 3/2007 | Szabo |
| 2007/0055573 A1 | 3/2007 | Grell |
| 2007/0059402 A1 | 3/2007 | Barmore |
| 2007/0118394 A1 | 5/2007 | Cahoon |
| 2007/0191689 A1 | 8/2007 | Elitok |
| 2007/0209656 A1 | 9/2007 | Lee |
| 2007/0258048 A1 | 11/2007 | Pitchers |
| 2007/0269557 A1 | 11/2007 | Culver et al. |
| 2007/0294129 A1 | 12/2007 | Froseth et al. |
| 2007/0298147 A1 | 12/2007 | Haus |
| 2008/0058783 A1 | 3/2008 | Altshuler et al. |
| 2008/0059342 A1 | 3/2008 | Culver et al. |
| 2008/0077455 A1 | 3/2008 | Gilboa |
| 2008/0083825 A1 | 4/2008 | Yang et al. |
| 2008/0091705 A1 | 4/2008 | McBride et al. |
| 2008/0158543 A1 | 7/2008 | Puskas et al. |
| 2008/0171120 A1 | 7/2008 | Willett |
| 2008/0183588 A1 | 7/2008 | Agrawal et al. |
| 2008/0186175 A1 | 8/2008 | Stern |
| 2008/0195456 A1 | 8/2008 | Fitzpatrick et al. |
| 2008/0254449 A1 | 10/2008 | Plante |
| 2008/0275309 A1 | 11/2008 | Stivoric et al. |
| 2009/0029014 A1 | 1/2009 | Walter et al. |
| 2009/0065570 A1 | 3/2009 | Peters et al. |
| 2009/0070040 A1 | 3/2009 | Rabinovitch et al. |
| 2009/0099873 A1 | 4/2009 | Kurple |
| 2009/0157460 A1 | 6/2009 | Narayanaswamy |
| 2009/0177068 A1 | 7/2009 | Stivoric et al. |
| 2009/0202700 A1 | 8/2009 | Bunke et al. |
| 2009/0208607 A1 | 8/2009 | Bunke et al. |
| 2009/0232958 A1 | 9/2009 | Samoto et al. |
| 2009/0275002 A1 | 11/2009 | Hoggle |
| 2009/0276912 A1 | 11/2009 | Sherman et al. |
| 2009/0278685 A1 | 11/2009 | Potyrailo et al. |
| 2009/0282004 A1 | 11/2009 | Williams |
| 2009/0283517 A1 | 11/2009 | MacKay et al. |
| 2009/0286212 A1 | 11/2009 | Gordon |
| 2009/0288606 A1 | 11/2009 | Zimmerman |
| 2010/0055653 A1 | 3/2010 | Miller-Kovach et al. |
| 2010/0076585 A1 | 3/2010 | Mayer et al. |
| 2010/0097193 A1 | 4/2010 | Tang |
| 2010/0102959 A1 | 4/2010 | Ashrafzadeh et al. |
| 2010/0106625 A1 | 4/2010 | McCoy |
| 2010/0106626 A1 | 4/2010 | Ashrafzadeh et al. |
| 2010/0117819 A1 | 5/2010 | Murray |
| 2010/0119659 A1 | 5/2010 | Ovadia et al. |
| 2010/0135211 A1 | 6/2010 | Park et al. |
| 2010/0152687 A1 | 6/2010 | Carlozzi |
| 2010/0175886 A1 | 7/2010 | Bohacs et al. |
| 2010/0198605 A1 | 8/2010 | Saulet |
| 2010/0216098 A1 | 8/2010 | Montgomery |
| 2010/0216136 A1 | 8/2010 | Man et al. |
| 2010/0218044 A1 | 8/2010 | Roblett et al. |
| 2010/0228160 A1 | 9/2010 | Schweizer |
| 2010/0268658 A1 | 10/2010 | Medo et al. |
| 2010/0280895 A1 | 11/2010 | Mottola |
| 2010/0287101 A1 | 11/2010 | Ishikawa et al. |
| 2011/0029364 A1 | 2/2011 | Roeding et al. |
| 2011/0082711 A1 | 4/2011 | Poeze et al. |
| 2011/0124096 A1 | 5/2011 | Philipak et al. |
| 2011/0197827 A1 | 8/2011 | Chang |
| 2011/0204137 A1 | 8/2011 | Scharfenort et al. |
| 2011/0217205 A1 | 9/2011 | Peeters |
| 2011/0236862 A1 | 9/2011 | Culver et al. |
| 2011/0258130 A1 | 10/2011 | Grabiner et al. |
| 2011/0259960 A1 | 10/2011 | Baarman et al. |
| 2011/0301441 A1 | 12/2011 | Bandic et al. |
| 2011/0302050 A1 | 12/2011 | Kildevaeld |
| 2011/0318717 A1 | 12/2011 | Adamowicz |
| 2012/0004935 A1 | 1/2012 | Winkler |
| 2012/0005105 A1 | 1/2012 | Beier et al. |
| 2012/0009550 A1 | 1/2012 | Gayle |
| 2012/0016814 A1 | 1/2012 | Evans |
| 2012/0027897 A1 | 2/2012 | Innocenzi |
| 2012/0052162 A1 | 3/2012 | Goulart |
| 2012/0055718 A1 | 3/2012 | Chen |
| 2012/0083669 A1 | 4/2012 | Abujbara |
| 2012/0085828 A1 | 4/2012 | Ziegler |
| 2012/0085829 A1 | 4/2012 | Ziegler |
| 2012/0105424 A1 | 5/2012 | Lee et al. |
| 2012/0135455 A1 | 5/2012 | Nerin De La Puerta et al. |
| 2012/0169469 A1 | 7/2012 | Butler et al. |
| 2012/0173269 A1 | 7/2012 | Omidi |
| 2012/0179665 A1 | 7/2012 | Baarman et al. |
| 2012/0199643 A1 | 8/2012 | Minnick et al. |
| 2012/0203572 A1 | 8/2012 | Christensen |
| 2012/0216911 A1 | 8/2012 | Bartholomew et al. |
| 2012/0251663 A1 | 10/2012 | Prins et al. |
| 2012/0274470 A1 | 11/2012 | Sandvick |
| 2012/0290051 A1 | 11/2012 | Boyden et al. |
| 2012/0315609 A1 | 12/2012 | Miller-Kovach et al. |
| 2012/0321759 A1 | 12/2012 | Marinkovich et al. |
| 2013/0033031 A1 | 2/2013 | Key |
| 2013/0048736 A1 | 2/2013 | Wien |
| 2013/0048737 A1 | 2/2013 | Baym et al. |
| 2013/0052616 A1 | 2/2013 | Silverstein et al. |
| 2013/0080784 A1 | 3/2013 | Oertli |
| 2013/0105565 A1 | 5/2013 | Kamprath |
| 2013/0117310 A1 | 5/2013 | Chai et al. |
| 2013/0209615 A1 | 8/2013 | Lee et al. |
| 2013/0231711 A1 | 9/2013 | Kaib |
| 2013/0269297 A1 | 10/2013 | Minvielle |
| 2013/0269454 A1 | 10/2013 | Minvielle |
| 2013/0269537 A1 | 10/2013 | Minvielle |
| 2013/0269538 A1 | 10/2013 | Minvielle |
| 2013/0269542 A1 | 10/2013 | Minvielle |
| 2013/0269543 A1 | 10/2013 | Minvielle |
| 2013/0269544 A1 | 10/2013 | Minvielle |
| 2013/0270337 A1 | 10/2013 | Minvielle |
| 2013/0273217 A1 | 10/2013 | Minvielle |
| 2013/0273222 A1 | 10/2013 | Minvielle |
| 2013/0273507 A1 | 10/2013 | Minvielle |
| 2013/0273509 A1 | 10/2013 | Mutti |
| 2013/0275037 A1 | 10/2013 | Minvielle |
| 2013/0275318 A1 | 10/2013 | Minvielle |
| 2013/0275342 A1 | 10/2013 | Minvielle |
| 2013/0275343 A1 | 10/2013 | Minvielle |
| 2013/0275370 A1 | 10/2013 | Minvielle |
| 2013/0275426 A1 | 10/2013 | Minvielle |
| 2013/0275439 A1 | 10/2013 | Minvielle |
| 2013/0275460 A1 | 10/2013 | Minvielle |
| 2013/0275477 A1 | 10/2013 | Minvielle |
| 2013/0276644 A1 | 10/2013 | Minvielle |
| 2013/0290364 A1 | 10/2013 | Minvielle |
| 2013/0295532 A1 | 11/2013 | Minvielle |
| 2013/0297642 A1 | 11/2013 | Minvielle |
| 2013/0309138 A1 | 11/2013 | Minvielle |
| 2013/0309636 A1 | 11/2013 | Minvielle |
| 2013/0309637 A1 | 11/2013 | Minvielle |
| 2013/0310955 A1 | 11/2013 | Minvielle |

(56) References Cited

U.S. PATENT DOCUMENTS

| | | |
|---|---|---|
| 2013/0337516 A1 | 12/2013 | Herrema |
| 2014/0018636 A1 | 1/2014 | Contant et al. |
| 2014/0037805 A1 | 2/2014 | Minvielle |
| 2014/0038140 A1 | 2/2014 | Minvielle |
| 2014/0041532 A1 | 2/2014 | Minvielle |
| 2014/0041533 A1 | 2/2014 | Minvielle |
| 2014/0061296 A1 | 3/2014 | Minvielle |
| 2014/0069838 A1 | 3/2014 | Minvielle |
| 2014/0191025 A1 | 7/2014 | Minvielle |
| 2014/0214714 A1 | 7/2014 | Minvielle |
| 2014/0236359 A1 | 8/2014 | Minvielle |
| 2014/0290395 A1 | 10/2014 | Minvielle |
| 2014/0290396 A1 | 10/2014 | Minvielle |
| 2014/0364971 A1 | 12/2014 | Minvielle |
| 2014/0364972 A1 | 12/2014 | Minvielle |
| 2015/0012122 A1 | 1/2015 | Minvielle |
| 2015/0017252 A1 | 1/2015 | Garland et al. |
| 2015/0037764 A1 | 2/2015 | Minvielle |
| 2015/0051841 A1 | 2/2015 | Minvielle |
| 2015/0057773 A1 | 2/2015 | Minvielle |
| 2015/0100462 A1 | 4/2015 | Minvielle |

FOREIGN PATENT DOCUMENTS

| | | |
|---|---|---|
| EP | 1 253 203 A1 | 10/2002 |
| FR | 2 813 683 A1 | 3/2002 |
| GB | 2 312 054 A | 10/1997 |
| WO | WO 91/13304 A1 | 9/1991 |
| WO | WO 02/06984 A2 | 1/2002 |
| WO | WO 02/37375 A1 | 5/2002 |
| WO | WO 2007/108906 A2 | 9/2007 |
| WO | WO 2008/054231 A1 | 5/2008 |
| WO | WO 2013/126579 A1 | 8/2013 |
| WO | WO 2013/134325 A1 | 9/2013 |
| WO | WO 2013/134544 A1 | 9/2013 |
| WO | WO 2013/142218 A1 | 9/2013 |
| WO | WO 2013/158571 A2 | 10/2013 |
| WO | WO 2013/158572 A2 | 10/2013 |
| WO | WO 2013/158576 A1 | 10/2013 |
| WO | WO 2013/176800 A1 | 11/2013 |
| WO | WO 2013/180925 A2 | 12/2013 |
| WO | WO 2014/168844 A2 | 10/2014 |
| WO | WO 2014/182566 A2 | 11/2014 |
| WO | WO 2014/210531 A2 | 12/2014 |
| WO | WO 2015/006351 A1 | 1/2015 |
| WO | WO 2015/013030 A1 | 1/2015 |
| WO | WO 2015/013031 A2 | 1/2015 |
| WO | 2015/069325 A1 | 5/2015 |
| WO | 2015/069950 A1 | 5/2015 |
| WO | 2015/073569 A1 | 5/2015 |

OTHER PUBLICATIONS

Office Action in U.S. Appl. No. 13/485,866, dated May 7, 2015.
Office Action in U.S. Appl. No. 13/485,883, dated May 20, 2015.
Office Action in U.S. Appl. No. 13/485,916, dated Mar. 27, 2015.
Office Action in U.S. Appl. No. 13/646,632, dated Mar. 26, 2015.
Office Action in U.S. Appl. No. 13/685,575, dated May 5, 2015.
Office Action in U.S. Appl. No. 13/888,353, dated Mar. 26, 2015.
Notice of Allowance in U.S. Appl. No. 13/921,078, dated Apr. 1, 2015.
Notice of Allowance in U.S. Appl. No. 13/931,733, dated Jun. 11, 2015.
Notice of Allowance in U.S. Appl. No. 14/044,851, dated Mar. 31, 2015.
Office Action in U.S. Appl. No. 14/203,353, dated Mar. 31. 2015.
Office Action in U.S. Appl. No. 14/260,115, dated Apr. 16, 2015.
Office Action in U.S. Appl. No. 14/466,805, dated Apr. 13, 2015.
Office Action in U.S. Appl. No. 14/286,627, dated Apr. 24, 2015.
Office Action in U.S. Appl. No. 14/466,824, dated May 7, 2015.
Office Actio in U.S. Appl. No. 14/467,433, dated May 8, 2015.
Notice of Allowance in U.S. Appl. No. 14/306,111, dated Mar. 17, 2015.

PCT International Search Report and Written Opinion in International Application No. PCT/US2014/044700, dated May 18, 2015.
PCT International Search Report and Written Opinion in International Application No. PCT/US2014/065281, dated Mar. 13, 2015.
Aernecke, M.J. et al., "Optical-fiber Arrays for Vapor Sensing", Sensors and Actuators B: Chemical, Nov. 2009, vol. 142, Issue 2, pp. 464-469.
Anslyn, E.V., "Supramolecular Analytical Chemistry", The Journal of Organic Chemistry, Feb. 2, 2007, vol. 72, No. 3, pp. 687-699.
Arora, P. et al., "An overview of transducers as platform for the rapid detection of foodborne pathogens", Appl. Microbial. Biotechnol., vol. 97, Issue 5, pp. 1829-1840, Jan. 18, 2013 (Published online).
"Automated Fruit Recognition" Fraunhofer, accessed online Nov. 13, 2014 and, available at http://www.iosb.fraunhofer.de/servlet/is/33328/.
Bell, S. et al., "Report on nutrient losses and gains factors used in European food composition databases", Technical Report, Apr. 2006, 66 pages (Retrieved from the Internet on Mar. 2, 2015 at: http://www.eurofir.net).
Chaudhry, Q. et al., "Applications and Implications of Nanotechnologies for the Food Sector", Food Additives and Contaminants: Part A, Mar. 2008, vol. 25, Issue 3, pp. 241-258.
Cheftel, J. Claude, "Food and Nutrition Labelling in the European Union", Food Chemistry 93.3, Dec. 2005, pp. 531-550, retrieved on Mar. 10, 2013 from URL: <http://www.sciencedirect.com/science/article/pii/S0308814604008581>.
Chung, I-C. et al., "A Portable Electrochemical Sensor for Caffeine and (−) Epigallocatechin Gallate Based on Molecularly Imprinted Poly(ethylene-co-vinyl alcohol) Recognition Element", J Nanosci Nanotechnol., vol. 11, No. 12, Dec. 2011, pp. 10633-10638.
"Cool runnings needed for fine wines," AFP, Apr. 28, 2008, retrieved from internet URL http://www.google.com/hostednews/afp/article/ALeqM5hm5gRK3maWqEJppJOBObR71THV on Feb. 10, 2014.
Composition of Foods Raw, Processed, Prepared USDA National Nutrient Database for Standard Reference, Release 26 Documentation and User Guide, U.S. Department of Agriculture Agricultural Research Service, Aug. 2013 (revised Nov. 2013), 136 pages, accessed on its website, at http://www.ars.usda.gov/SP2UserFiles/Place/12354500/Data/SR26/sr26_doc.pdf.
De Vos, K. et al., "Multiplexed antibody detection with an array of silicon-on-insulator microring resonators", IEEE, Photonics Journal, vol. 1, Issue 4, Oct. 2009, pp. 225-235.
Diller, K.R., "Stress Protein Expression Kinetics", Annual Review of Biomedical Engineering, 2006, vol. 8, pp. 403-424.
Dorokhin, D. et al., "Imaging surface plasmon resonance for multiplex microassay sensing of mycotoxins", Analytical and Bioanalytical Chemistry, vol. 400, Issue 9, published online Apr. 12, 2011, pp. 3005-3011.
Ebarvia, et al, "Biomimetic piezoelectric quartz sensor for caffeine based on a molecularly imprinted polymer", Analytical and Bioanalytical Chemistry, vol. 378, Issue 5, Mar. 2004, published online Jan. 27, 2004, pp. 1331-1337.
Etherington, Darrell, "iCarte Turns the iPhone Into an RFID Reader," Gigaom, Nov. 18, 2009 (downloaded Oct. 3, 2013, from URL http://gigaom.com/2009/11/18/icarte-turns-the-iphone-into-an-rfid-reader/).
Focke, M. et al., "Lab-on-a-Foil: microfluidics on thin and flexible films", Lab on a Chip, vol. 10, Issue 11, published online Mar. 19, 2010, pp. 1365-1386.
Frankel, E.N., "Chemistry of Extra Virgin Olive Oil: Adulteration, Oxidative Stability, and Antioxidants", Journal of Agricultural and Food Chemistry, 2010, vol. 58 (10), pp. 5991-6006.
Garcia-Gonzalez, D.L. et al., "Research in Olive Oil: Challenges for the Near Future", Journal of Agricultural and Food Chemistry, 2010, vol. 58, Issue 24, pp. 12569-12577.
Gartia, M. et al., "Colorimetric plasmon resonance imaging using nano lycurgus cup arrays", Advanced Optical Materials, vol. 1, Issue 1, Jan. 2013, pp. 68-76.
Ghasemi-Varnamkhasti, M. et al., "Biomimetric-based odor and taste sensing systems to food quality and safety characterization: An overview on basic principles and recent achievements", Journal of Food Engineering, vol. 100, Issue 3, Oct. 2010, pp. 377-387.

(56) References Cited

OTHER PUBLICATIONS

Grate, J.W., "Acoustic Wave Microsensor Arrays for Vapor Sensing", Chemical Reviews, 2000, vol. 100, No. 7, pp. 2627-2647.
Greenfield, H. et al., "Food composition data," FAO, 2003 ("FAO").
Hayano-Kanashiro, C. et al., "Analysis of Gene Expression and Physiological Responses in Three Mexican Maize Landraces Under Drought Stress and Recovery Irrigation", PLoS One, Oct. 2009, vol. 4, Issue 10, e7531, pp. 1-19.
Hierlemann, A. et al., "Higher-Order Chemical Sensing", Chemical Reviews, 2008, vol. 108, No. 2, pp. 563-613.
Hoffman, B., "IBM Announces Food Traceability Technology", Food+Tech Connect, Oct. 19, 2011, 2 pages.
Hsieh, M-D. et al., "Limits of Recognition for Simple Vapor Mixtures Determined with a Microsensor Array", Analytical Chemistry, Apr. 1, 2004, vol. 76, No. 7, pp. 1885-1895.
Huang, et al., "A passive radiofrequency pH sensing tag for wireless food quality monitoring", IEEE Sensors Journal, vol. 12, Issue 3, Mar. 2012, pp. 487-495.
Hugh, J. "Recipe Calculations: Where Do We Stand?", Proceedings of the 12th National Nutrient Databank Conference, Houston, Texas, Apr. 12, 1987, pp. 135-139 (Retrieved from the Internet on Feb. 13, 2015 at http://www.nutrientdataconf.org/PastConf/NDBC12/5-2_Joseph.pdf).
James, D. et al., "Chemical Sensors for Electronic Nose Systems", Microchimica Acta, Feb. 2005, vol. 149, pp. 1-17.
Janata, J. et al., "Conducting Polymers in Electronic Chemical Sensors", Nature Materials, Jan. 2003, vol. 2, pp. 19-24.
Kaume, L. et al., "The Blackberry Fruit: A Review on Its Composition and Chemistry, Metabolism and Bioavailability, and Health Benefits", Journal of Agricultural and Food Chemistry, 2012, vol. 60 (23), pp. 5716-5727.
Kharif, Olga, "Janne Haverinen: Mapping the Great Indoors", Bloomberg BusinessWeek, May 9, 2012, retrieved from URL: <http://www.businessweek.com/articles/2012-08-09/janne-haverinen-mapping-the-great-indoors on Apr. 12, 2013>.
Kingsmore, S.F., "Multiplexed Protein Measurement: Technologies and Applications of Protein and Antibody Arrays", Nature Reviews Drug Discovery, Apr. 2006, vol. 5, pp. 310-321.
Kumar, A. et al., "Study of fiber optic sugar sensor", Pramana, vol. 67, Issue 2, Aug. 2006, pp. 383-387.
Kwon, H. et al., "Fluorescent DNAs printed on paper: Sensing food spoilage and ripening in the vapor phase", Chemical Science, vol. 3, Issue 8, published online May 17, 2012, pp. 2542-2549.
Lago, F.C. et al., "FINS Methodology to Identification of Sardines and Related Species in Canned Products and Detection of Mixture by Means of SNP Analysis Systems", European Food Research and Technology, Jun. 2011, vol. 232(6), pp. 1077-1086.
Lago, F.C. et al., "Genetic Identification of Horse Mackerel and Related Species in Seafood Products by Means of Forensically Informative Nucleotide Sequencing Methodology", Journal of Agricultural and Food Chemistry, 2011, vol. 59 (6), pp. 2223-2228.
Lewis, N.S., "Comparisons Between Mammalian and Artificial Olfaction Based on Arrays of Carbon Black-Polymer Composite Vapor Detectors", Accounts of Chemical Research, 2004, vol. 37, No. 9, pp. 663-672.
Lin, et al., "Multiplex fiber-optic biosensor using multiple particle plasmon resonances", International Society for Optics and Photonics: Third Asia Pacific Optical Sensors Conference, vol. 8351, Sydney, Australia, Jan. 31, 2012, pp. 83512S1-83512S7.
Martins-Lopes, P. et al., "DNA Markers for Portuguese Olive Oil Fingerprinting", Journal of Agricultural and Food Chemistry, 2008, vol. 56 (24), pp. 11786-11791.
Montealegre, C. et al., "Traceability Markers to the Botanical Origin in Olive Oils", Journal of Agricultural and Food Chemistry, 2010, vol. 58, Issue 1, pp. 28-38.
Montesinos, E., "Plant-associated Microorganisms: a View from the Scope of Microbiology", International Microbiology, 2003, vol. 6, Issue 4, pp. 221-223.

Ni, et al., "Gene Expression and Regulation of Higher Plants Under Soil Water Stress", Current Genomics, Jun. 2009, vol. 10, pp. 269-280.
Perks, B., "Fighting Food Fraud with Science", Text Reproduced from Chemistry World, 2007, vol. 4, Issue 9, pp. 48-52.
Preechaburana, et al., "Surface Plasmon Resonance Chemical Sensing on Cell Phones", Angewandte Chemie International Edition, vol. 51, Issue 46, pp. 11585-11588, first published online Oct. 16, 2012.
Primrose, S. et al., "Food Forensics: Methods for Determining the Authenticity of Foodstuffs", Trends in Food Science & Technology, Dec. 2010, vol. 2, Issue 12, pp. 582-590.
Rashidi, L. et al., "The Applications of Nanotechnology in Food Industry", Critical Reviews in Food Science and Nutrition, 2011, vol. 51, Issue 8, pp. 723-730.
Ricci, F. et al., "A review on novel developments and applications of immunosensors in food analysis", Analytica Chimica Acta, vol. 605, Issue 2, Dec. 19, 2007, pp. 111-129.
Roche, PJR, et al., "A Camera Phone Localised Surface Plasmon Biosensing Platform Towards Low-Cost Label-Free Diagnostic Testing", Journal of Sensors, vol. 2011, 2011, 7 pages.
Röck, F. et al., "Electronic Nose: Current Status and Future Trends", Chemical Reviews, 2008, vol. 108, No. 2, pp. 705-725.
Scampicchio, M. et al., "Optical nanoprobes based on gold nanoparticles for sugar sensing", Nanotechnology, vol. 20, Issue 13, Apr. 1, 2009, 5 pages.
Sinclair, D.A. et al., "Unlocking the Secrets of Longevity Genes", Scientific AmErikan, Mar. 2006, vol. 294, Issue 3, pp. 48-57.
"SIRA Technologies Food Sentinel System Thermal Barcode for Packaging", Sustainable is Good: Lifestyle and Design Blog, Mar. 4, 2009, 2 pages.
Srinivas, P.R. et al., "Nanotechnology Research: Applications in Nutritional Sciences", The Journal of Nutrition, Symposium-Nanotechnology Research: Applications in Nutritional Sciences, Jan. 2010, vol. 140, No. 1, pp. 119-124.
Staggers, N. et al., "Nanotechnology: The Coming Revolution and its Implications for Consumers, Clinicians, and Informatics", Nursing Outlook, Sep.-Oct. 2008, vol. 56, No. 5, pp. 268-274.
Suslick, B.A. et al., "Discrimination of Complex Mixtures by a Colorimetric Sensor Array: Coffee Aromas", Analytical Chemistry, Mar. 1, 2010, vol. 82, No. 5, pp. 2067-2073.
Thakur, M. et al., "Food Traceability, R&D in Norway", Food Technology, Apr. 2012, p. 42-46.
Valero, C., et al., "Design Guidelines for a Quality Assessment System of Fresh Fruits in Fruit Centers and Hypermarkets", Abstract, Agriculture Engineering International: the CIGR Journal of Scientific Research and Development, vol. II, Aug. 2000, 20 pages. Available online at http://dspace.library.cornell.edu/retrieve/237/, accessed Feb. 19, 2015.
Walt, D.R., "Electronic Noses: Wake Up and Smell the Coffee", Analytical Chemistry, Feb. 1, 2005, vol. 77, Issue 3, p. A-45.
Wolfbeis, O.S., "Materials for Fluorescence-based Optical Chemical Sensors", Journal of Materials Chemistry, 2005, vol. 15, pp. 2657-2669.
Zerebecki, R.A. et al., "Temperature Tolerance and Stress Proteins as Mechanisms of Invasive Species Success", PLoS One, Apr. 2011, vol. 6, Issue 4, e14806, pp. 1-7.
Zhu, H. et al., "Quantum dot enabled detection of *Escherichia coli* using a cell-phone", ANALYST, vol. 137, Issue 11, Jun. 7, 2012, pp. 2541-2544.
Zou, M-Q et al., "Rapid Authentication of Olive Oil Adulteration by Raman Spectrometry", Journal of Agricultural and Food Chemistry, 2009, vol. 57, Issue 14, pp. 6001-6006.
Office Action in U.S. Appl. No. 13/485,850, dated May 9, 2013.
Office Action in U.S. Appl. No. 13/485,850, dated Sep. 30, 2013.
Office Action in U.S. Appl. No. 13/485,850, dated Mar. 20, 2014.
Office Action in U.S. Appl. No. 13/485,850, dated Sep. 29, 2014.
Office Action in U.S. Appl. No. 13/485,863, dated Feb. 9, 2015.
Office Action in U.S. Appl. No. 13/485,878, dated Oct. 24, 2013.
Office Action in U.S. Appl. No. 13/485,878, dated Jun. 5, 2014.
Advisory Action in U.S. Appl. No. 13/485,878, dated Sep. 16, 2014.
Office Action in U.S. Appl. No. 13/485,883, dated Feb. 3, 2015.
Office Action in U.S. Appl. No. 13/485,900, dated Feb. 3, 2015.

(56) References Cited

OTHER PUBLICATIONS

Office Action in U.S. Appl. No. 13/560,965, dated Feb. 1, 2013.
Notice of Allowance in U.S. Appl. No. 13/560,965, dated Mar. 22, 2013.
Office Action in U.S. Appl. No. 13/602,040, dated Oct. 23, 2013.
Office Action in U.S. Appl. No. 13/602,040, dated Jul. 17, 2014.
Office Action in U.S. Appl. No. 13/685,575, dated May 6, 2013.
Office Action in U.S. Appl. No. 13/685,575, dated Oct. 24, 2013.
Office Action in U.S. Appl. No. 13/685,575, dated Oct. 27, 2014.
Office Action in U.S. Appl. No. 13/684,113, dated Dec. 15, 2014.
Office Action in U.S. Appl. No. 13/729,548, dated Dec. 2, 2014.
Office Action in U.S. Appl. No. 13/732,050, dated Oct. 24, 2013.
Office Action in U.S. Appl. No. 13/732,050, dated Apr. 10, 2014.
Office Action in U.S. Appl. No. 13/750,804, dated Mar. 12, 2013.
Notice of Allowance in U.S. Appl. No. 13/750,804, dated May 31, 2013.
Office Action in U.S. Appl. No. 13/771,004, dated May 15, 2013.
Office Action in U.S. Appl. No. 13/771,004, dated Jul. 8, 2013.
Office Action in U.S. Appl. No. 13/771,004, dated Apr. 4, 2014.
Office Action in U.S. Appl. No. 13/771,004, dated Mar. 10, 2015.
Office Action in U.S. Appl. No. 13/900,426, dated Aug. 8, 2013.
Notice of Allowance in U.S. Appl. No. 13/900,426, dated Dec. 16, 2013.
Office Action in U.S. Appl. No. 13/861,300 dated Feb. 24, 2015.
Office Action in U.S. Appl. No. 13/888,353, dated May 1, 2014.
Office Action in U.S. Appl. No. 13/888,353, dated Oct. 1, 2014.
Office Action in U.S. Appl. No. 13/921,078, dated Nov. 4, 2014.
Office Action in U.S. Appl. No. 13/931,733, dated Nov. 6, 2014.
Office Action in U.S. Appl. No. 13/931,733, dated Mar. 10, 2015.
Office Action in U.S. Appl. No. 13/931,744, dated Aug. 20, 2013.
Notice of Allowance in U.S. Appl. No. 13/931,744, dated Feb. 28, 2014.
Office Action in U.S. Appl. No. 13/937,167, dated Oct. 28, 2013.
Office Action in U.S. Appl. No. 13/937,167, dated Apr. 14, 2014.
Office Action in U.S. Appl. No. 13/948,004, dated Oct. 24, 2013.
Office Action in U.S. Appl. No. 13/948,004, dated Jun. 11, 2014.
Office Action in U.S. Appl. No. 14/044,851, dated Jan. 5, 2015.
Office Action in U.S. Appl. No. 14/047,817, dated Nov. 29, 2013.
Notice of Allowance in U.S. Appl. No. 14/047,817, dated Apr. 14, 2014.
Office Action in U.S. Appl. No. 14/059,441, dated Feb. 11, 2014.
Office Action in U.S. Appl. No. 14/059,441, dated Jul. 10, 2014.
Notice of Allowance in U.S. Appl. No. 14/059,441, dated Jan. 5, 2015.
Office Action in U.S. Appl. No. 14/074,664, dated Jan. 8, 2014.
Notice of Allowance in U.S. Appl. No. 14/074,664, dated Jun. 2, 2014.
Office Action in U.S. Appl. No. 14/137,963, dated Aug. 5, 2014.
Notice of Allowance in U.S. Appl. No. 14/137,963, dated Jan. 28, 2015.
Office Action in U.S. Appl. No. 14/304,671, dated Feb. 4, 2015.
Office Action in U.S. Appl. No. 14/306,111, dated Nov. 13, 2014.
Office Action in U.S. Appl. No. 29/497,888, dated Nov. 19, 2014.
PCT International Search Report and Written Opinion in International Application No. PCT/US2013/027148, dated Jun. 18, 2013.
PCT International Search Report and Written Opinion in International Application No. PCT/US2013/029219, dated Jun. 20, 2013.
PCT International Search Report and Written Opinion in International Application No. PCT/US2013/029686, dated May 13, 2013.
PCT International Search Report and Written Opinion in International Application No. PCT/US2013/031106, dated May 31, 2013.
PCT International Search Report and Written Opinion in International Application No. PCT/US2013/36666, dated Oct. 4, 2013.
PCT International Search Report and Written Opinion in International Application No. PCT/US2013/036668, dated Dec. 6, 2013.
PCT International Search Report and Written Opinion in International Application No. PCT/US2013/036670, dated Aug. 19, 2013.
PCT International Search Report and Written Opinion in International Application No. PCT/US2013/036673, dated Aug. 20, 2013.
PCT International Search Report and Written Opinion in International Application No. PCT/US2013/040445, dated Oct. 25, 2013.
PCT International Search Report and Written Opinion in International Application No. PCT/US2014/033084, dated Mar. 6, 2015.
PCT International Search Report and Written Opinion in International Application No. PCT/US2014/036570, dated Mar. 10, 2015.
PCT International Search Report and Written Opinion in International Application No. PCT/US2014/044696, dated Oct. 10, 2014.
PCT International Search Report and Written Opinion in International Application No. PCT/US2014/045796, dated Oct. 15, 2014.
PCT International Search Report and Written Opinion in International Application No. PCT/US2014/045798, dated Oct. 15, 2014.
PCT International Search Report and Written Opinion in International Application No. PCT/US2014/045807, dated Jan. 22, 2015.
PCT International Search Report and Written Opinion in International Application No. PCT/US14/59186, dated Dec. 22, 2014.
PCT International Search Report and Written Opinion in International Application No. PCT/US2014/064434, dated Feb. 20, 2015.
Statement in accordance with the Notice from the European Patent Office, dated Oct. 1, 2007, concerning business methods.
Notice from the European Patent Office, dated Oct. 1, 2007, concerning business methods, Official Journal EPO, pp. 592-593.
Extended European Search Report in European Application No. 13731655.0, dated Feb. 24, 2014.
Communication Pursuant to Article 94(3) in European Application No. 13731655.0, dated Jan. 22, 2015.
Extended European Search Report in European Application No. 13757669.0, dated Jan. 31, 2014.
European Examination Report in European Application No. 13757669.0, dated Oct. 13, 2014.
Extended European Search Report in European Application No. 13751912.0, dated Feb. 25, 2015.

* cited by examiner

SYSTEM FOR TRACKING AND OPTIMIZING HEALTH INDICES

RELATED APPLICATIONS

This application claims the benefit of, and priority to, U.S. Provisional Patent Application Ser. No. 61/888,451 filed Oct. 8, 2013, titled "SYSTEM FOR TRACKING AND OPTIMIZING HEALTH INDICES," the entire disclosure of which is incorporated herein by reference in its entirety.

FIELD OF THE INVENTION

The present invention generally relates to a system and method for tracking and optimizing health indices. More specifically, in some embodiments the present invention relates to a system and method for tracking and optimizing health indices of one or more individuals having a particular genetic profile and adaptively managing external factors the individual experiences so as to optimize a change in one or more health indices based on the individual's genetic profile.

BACKGROUND OF THE INVENTION

The cells, organs, systems, and bodies of living organism change over time, growing, improving, or degrading throughout the organism's existence, from birth to death or expiration. The progression of these changes describes a traceable change pattern across time for various aspects of the organism's health and wellbeing.

Scientific advancements have made the ability to determine an individual organism's genetic code a reality, and such information is increasingly utilized. Individuals and their health providers are becoming increasingly aware of the potential impact external factors such as nutrition, lifestyle and medicines have on their health. More recently, scientists are starting to consider wherein individuals with similar genetic codes, experiencing similar external factors, will be predisposed to experience similar health outcomes.

While there has recently been greater attention by consumer organizations, health organizations and the public to the nutritional value of nutritional substances, and the efficacy value of consumables and cosmetic substances, and the impact on health, the industries that provide such products have been slow in responding to this attention. Further, the concept of one's genetic profile playing a role in the real benefit received to an individual from such products, is extremely new, and information available to inform an individual is nearly nonexistent.

An information system allowing an individual organism of a particular genetic profile to adaptively manage major external factors that it may experience, particularly its consumption of nutritional substances and consumables and cosmetic substances, so as to optimize its $\Delta$Hs over time, would offer great benefit.

OBJECTS OF THE INVENTION

It is an object of the present invention to track and monitor the various aspects associated with the organism's health and wellbeing which can be qualitatively or quantitatively described by various health indices, wherein values associated with the state of each corresponding health index can be assigned. Such health index values can be tracked over time. Changes in these health index values are individually and collectively referred to herein as $\Delta$H.

Is it another object of the present invention to track and monitor individuals with a particular genetic code, and individuals with similar genetic codes, experiencing similar external factors, will be predisposed to experience similar $\Delta$Hs. As referred to herein, individuals with genetic traits that predispose them to experience similar $\Delta$Hs to other individuals experiencing similar external factors are said to share a similar genetic profile.

In an object of the present invention, an information system is provided with a genetic profile database containing $\Delta$H data for various genetic profiles, wherein each genetic profile includes $\Delta$H data for organisms with genetic traits that predispose them to experience similar $\Delta$Hs when experiencing similar external factors.

In a further object of the present invention, an information system is provided with a genetic profile database containing $\Delta$H data for various genetic profiles, wherein each genetic profile includes $\Delta$H data for organisms with genetic traits that predispose them to experience similar $\Delta$Hs when consuming similar nutritional substances and consumables and cosmetic substances.

In an object of the present invention, an information system and database are provided to track and store health index values and changes in the health index values ($\Delta$H).

In an object of the present invention, an information system is provided to adaptively manage major external factors that an individual organism having a particular genetic profile may experience, so as to optimize various $\Delta$Hs of the individual organism over time.

In a further object of the present invention, an information system is provided to adaptively manage consumption of nutritional substances and consumables and cosmetic substances an individual organism having a particular genetic profile may consume or use, so as to optimize various $\Delta$Hs of the individual organism over time.

SUMMARY OF THE INVENTION

Embodiments of the present invention relate generally to a system and method for tracking and optimizing health indices.

In some embodiments a system for tracking and/or optimizing one or more health indices associated with an individual is provided comprising: a genetic profile database that collects genetic code data for individuals and identifies corresponding genetic profiles based on the genetic code data; a $\Delta$H database that contains $\Delta$H data associated with each of the genetic profiles, the $\Delta$H data comprising changes in one or more health indices associated with an individuals' health; wherein an individual may track or adaptively manage external factors the individual experiences so as to optimize $\Delta$H based on the individual's particular genetic profile.

The one or more health indices may be comprised of quantitative or qualitative values or scores associated with quality of life, disease state, disease resistance, vital signs, blood chemistry, strength, endurance, metal elasticity, or other factors associated with an individuals' health or wellbeing.

In some embodiments the $\Delta$H database further contains information regarding nutritional values of nutritional substances and efficacy values of consumables and cosmetic substances, and combinations thereof, and such information is correlated to one or more of the health indices for a given genetic profile. Optionally, the $\Delta$H database further contains at least one $\Delta$N value, wherein $\Delta$N is the actual residual nutritional value of the nutritional substance an individual plans to prepare or consume, or a change in the nutritional value of the nutritional substance over time. According to embodiments of the present invention, $\Delta N$ is a change in a nutritional, organoleptic, or aesthetic value of the nutritional substance and said change comprises any of a maintenance, improvement, or degradation.

In another embodiment, the $\Delta H$ database further contains at least one $\Delta E$ value, wherein $\Delta E$ is the actual residual efficacy value of the consumables or cosmetics substances an individual plans to consume or use, or a change in the efficacy value of the consumables or cosmetics substances over time.

In a further aspect, embodiments of the present invention provide a system for tracking and optimizing health indices of one or more individuals, characterized in that: an individual having a particular genetic profile adaptively manages external factors the individual experiences so as to optimize a change in one or more health indices based on the individual's genetic profile.

BRIEF DESCRIPTION OF THE DRAWINGS

The accompanying drawing, which is incorporated in and constitute a part of this specification, exemplify the embodiments of the present invention and, together with the description, serve to explain and illustrate principles of the invention. The drawing is intended to illustrate major features of the exemplary embodiments in a diagrammatic manner. The drawing is not intended to depict every feature of actual embodiments nor relative dimensions of the depicted elements, and is not drawn to scale.

DETAILED DESCRIPTION

Embodiments of the present invention broadly provide a system and method for tracking and optimizing health indices. In some embodiments a system for tracking and/or optimizing one or more health indices associated with an individual is provided comprising: a genetic profile database that collects genetic code data for individuals and identifies corresponding genetic profiles based on the genetic code data; a $\Delta H$ database that contains $\Delta H$ data associated with each of the genetic profiles, the $\Delta H$ data comprising changes in one or more health indices associated with an individuals' health; wherein an individual may track or adaptively manage external factors the individual experiences so as to optimize $\Delta H$ based on the individual's particular genetic profile.

As described herein, various aspects associated with organism's or individual's health and wellbeing which can be qualitatively or quantitatively described by various health indices, is characterized as a health index, and wherein values associated with the state of each corresponding health index can be assigned. Such health index values can be tracked over time. Changes in these health index values are individually and collectively referred to herein as $\Delta H$.

Moreover, individuals with a particular genetic code, and individuals with similar genetic codes, experiencing similar external factors, will be predisposed to experience similar $\Delta H$s. As referred to herein, individuals with genetic traits that predispose them to experience similar $\Delta H$s to other individuals experiencing similar external factors are said to share a similar genetic profile.

Figure 1:
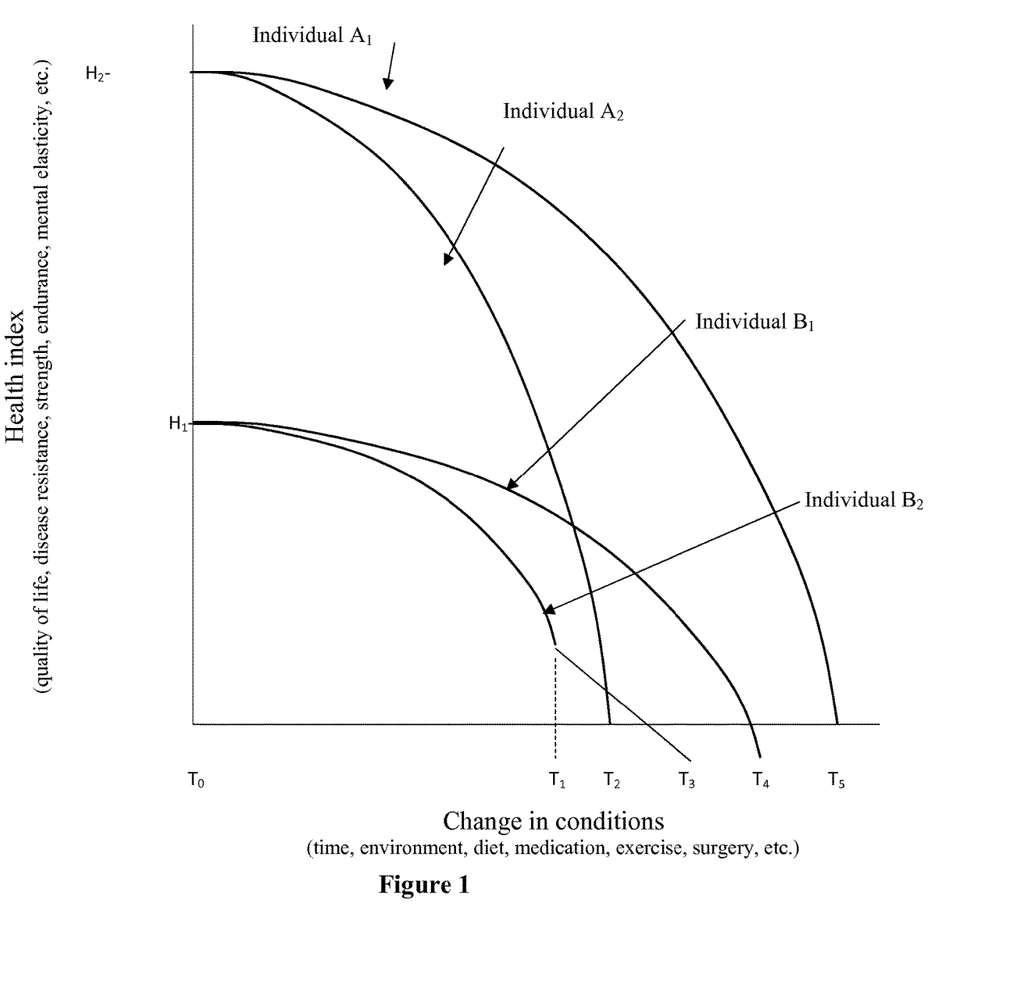
FIG. 1 is a graph illustrating a particular health index of three individuals plotted against various changes in conditions to which the individuals may be exposed according to embodiments of the present invention.

FIG. 1 shows a particular health index of three individuals plotted against various changes in conditions to which the individuals may be exposed. As used herein, the terms individual and individuals may also refer to individual organism and individual organisms, respectively. An individual's health indices may include quantitative or qualitative values, ratings, scores, and the like, assigned to various aspects associated with the individuals health and well being. Such health indices may include, but are not limited to, values associated with the quality of life, disease resitance, strength, endurance, mental elasticity, and any other factors associated with an individuals health and well being that can be quantitatively or qualitatively valued. Changes in such health indices are individually and collectively referred to herein as $\Delta H$.

Changes in conditions individuals may experience, or to which individuals may be exposed include, but are not limited to, changes in elapsed time, diet, medication, exercise, surgery, and any other change in condition which an individual may experience. Such changes in conditions may concurrently include any combination of changes in conditions to which the individuals may be exposed. For example, in one embodiment, changes in conditions concurrently include elapsed time and diet. In another embodiment, changes in conditions concurrently include elapsed time and medication. In a further embodiment, changes in conditions concurrently include elapsed time, diet, and medication. In a preferred embodiment, changes in conditions concurrently include elapsed time, residual nutritional values of nutritional substances consumed (referred to herein as $\Delta N$ information) and residual efficacy values of consumables and cosmetic substances used, including medications (referred to herein as $\Delta E$ information).

In FIG. 1, the line identified as "Individual $A_1$" represents a first individual having a particular genetic profile "A" and a corresponding initial particular health index value of "$H_2$". The line identified as "Individual $A_2$" represents a second individual having a similar genetic profile "A" and accordingly the same initial particular health index value of "$H_2$". The line identified as "Individual $B_1$" represents a third individual having a particular genetic profile "B" and a corresponding initial particular health index value of "$H_1$". The line identified as "Individual $B_2$" represents a forth individual having a similar genetic profile "B" and accordingly the same initial particular health index value of "$H_1$".

Individual $A_1$ has an initial particular health index value of H2 at $T_0$, for example at birth. Individual $A_1$, which includes those caring for him, has knowledge of his genetic code, "$a_1$", which may be determined in any fashion known to those skilled in the art, and can be stored in any format known to those skilled in the art. Individual A1 has access to a database corresponding to individuals with various genetic profiles. He may determine and access the genetic profile corresponding to his genetic code $a_1$ by transmitting his genetic code $a_1$ to the database, wherein the database identifies the corresponding genetic profile $A_1$. Each genetic profile contained within the database is referenced to information regarding nutritional values of nutritional substances and efficacy values of consumables and cosmetic substances, and combinations thereof, required to optimize various corresponding health indices for individuals with that genetic profile. Such a database is also referred to herein as an $\Delta H$ database. Individual $A_1$ additionally has access to information systems with databases containing information regarding the actual residual nutritional value of nutritional substances he plans to prepare or consume, also referred to herein as ΔN information, and the actual residual efficacy value of consumables and cosmetic substances he plans to consume or use, also referred to herein as ΔE information. Information systems and databases containing such ΔN and ΔE information are further described in detail in copending U.S. patent application Ser. Nos. 13/771,004, 13/888,353, 13/948,004, 13/948,078, 13/948,083, and 14/044,851, the teaching and descriptions of all of which are incorporated herein by reference in their entirety.

ΔN refers to the measurement, estimation, and tracking of changes to the nutritional content of a nutritional substance from creation to consumption. This ΔN information could be used, not only by the consumer in selecting nutritional substances to consume but could be used by the other food and beverage industry silos, including creation, preservation, transformation, and conditioning, to make decisions on how to create, handle and process nutritional substances. Additionally, those who sell nutritional substances to consumers, such as restaurants and grocery stores, could communicate perceived qualitative values of the nutritional substance in their efforts to market and position their nutritional substance products. Further, a determinant of price of the nutritional substance could be nutritional, organoleptic, or aesthetic values, and if changes to those values, also referred to herein as ΔN, are perceived as desirable. For example, if a desirable value has been maintained, improved, or minimally degraded, it could be marketed as a premium product. ΔE refers to the change in efficacy values of consumables and cosmetic substances. While the consumables and cosmetic substance industry can be composed of many companies or businesses, it can also be integrated into combinations of business serving many roles or can be one business or even individual. Since ΔE is a measure of the change in an efficacy value of a corresponding consumables and cosmetic substance, knowledge of a prior efficacy value (also referred to as prior efficacy state) of a consumables and cosmetic substance and the ΔE value will provide knowledge of the residual efficacy value (also referred to as current efficacy value or current efficacy state).

ΔE information for the consumables and cosmetic substance may be stored in a dynamic efficacy value database. The database may also contain sensed physical attribute values for known consumables and cosmetic substances at known efficacy states, also referred to herein as a consumables and cosmetic substance attribute library. The consumables and cosmetic substance attribute library can be utilized for determining the identity and current efficacy state of a consumables and cosmetic substance. The database can be connected to the other modules by a variety of communication systems, such as paper, computer networks, the internet and telecommunication systems, such as wireless telecommunication systems. In a system capable of receiving and processing real time consumer feedback and updates regarding changes in an efficacy value of a corresponding consumables and cosmetic substance, or ΔE, consumers can even play a role in updating the dynamic efficacy value database with observed or measured information about the consumables and cosmetic substances they have purchased and/or dispensed for consumption and/or consumed, so that the information is available and useful to determine a corresponding ΔE, and may further be available to others in the consumables and cosmetic substance supply system.

The ΔH database containing information regarding nutritional values of nutritional substances and efficacy values of consumables and cosmetic substances, and combinations thereof, required to optimize a particular health index for individuals with known genetic profiles, can be utilized to adaptively recommend the consumption or use of particular nutritional substances and consumables and cosmetic substances responsive to: an individual's genetic code; tracked information regarding actual residual nutritional and efficacy values of nutritional substances and consumables and cosmetic substances already consumed or used by an individual; and ΔN and ΔE information for nutritional substances and consumables and cosmetic substances currently being considered by the individual.

In an example, individual A1 utilizes information regarding his genetic code "a1" to identify a corresponding genetic profile in the AH database, wherein the corresponding genetic profile "A" is referenced to information regarding nutritional values of nutritional substances and efficacy values of consumables and cosmetic substances, and combinations thereof, required to optimize particular health indices for individuals with genetic profile "A". Input from individual A1 may also include one or more particular health indices of interest, and may further include information regarding the actual residual nutritional and efficacy values of nutritional substances and consumables and cosmetic substances already consumed or used individual A1, wherein such information may have been acquired through his use of the information systems such as described in detail in copending U.S. patent application Ser. Nos. 13/771,004, 13/888,353, 13/948,004, 13/948,078, 13/948,083, and 14/044,851, the teaching and descriptions of all of which are incorporated herein by reference in their entirety. For example, a consumer interface provided with, or communicating with, a local storage container may enable the local storage container to communicate to the consumer that it contains consumables and cosmetic substance, information related to its ΔE, including current residual efficacy values. Information regarding the dynamically-labeled nutritional substances from each stage of the production of the nutritional substances from creation to consumption may be collected, tracked, and organized. The information regarding the dynamically-labeled nutritional substances may be openly available and openly integrated at any point in time. The integration and availability of the information may be enabled by dynamic labeling provided with the nutritional substances, which includes a unique nutritional substance identifier.

Responsive to the input from individual A1, the AH database adaptively determines and provide recommendations regarding current needs for consumption or use of nutritional substances and consumables and cosmetic substances so as to optimize corresponding health indices. The adaptive nature of such recommendations takes into account deficient, proper, or excesses levels of particular nutritional values and efficacy values. For example, the input regarding the actual residual nutritional and efficacy values of nutritional substances and consumables and cosmetic substances already consumed or used by individual A1 may compared to, or otherwise evaluated against, the AH database for genetic profile "A", in order to determine currently needed levels of corresponding nutritional and efficacy values. Using the adaptively determined recommendations from the AH database regarding needed nutritional and efficacy values, individual A1 can further utilize the information systems described fully and in detail in copending U.S. patent application Ser. Nos. 13/771,004, 13/888,353, 13/948,004, 13/948,078, 13/948,083, and 14/044,851 to accomplish conditioning, dispensing, consumption, and use of nutritional substances and consumables and cosmetic substances to assure the consumption and use of required residual nutritional and efficacy values. For example, a dispensing module may be used to dispense consumables and cosmetic substances immediately before consumption. The dispensing module may include, but is not limited to, a volumetric-based dispensing system, a weight-based dispensing machine, a counting device, a controlled storage environment, a storage container tracking storage conditions such as temperature, an individual such as a doctor, pharmacist, nurse, patient, etc. It may also be systems used by commercial establishments to prepare consumables and cosmetic substance for consumers, such as equipment used by a hospital or a compounding pharmacy, or other devices located at businesses which provide consumables and cosmetic substances to consumers. Such consumables and cosmetic substances could be for consumption at the business or for the consumer to take out from the business. The dispensing module can also be any combination of these systems, machines, devices, equipment, or individuals used to dispense consumables and cosmetic substances for consumption by consumers. A consumption module may be implemented to select consumables and cosmetic substances according to $\Delta E$ information and residual efficacy values. This will further allow consumers to make informed decisions regarding consumables and cosmetic substance additives, preservatives, origins, traceability, and other consumables and cosmetic substance attributes that may also be tracked through an information module. Furthermore, the consumption module may provide information for the consumer to operate the dispensing module with adaptive dispensing parameters, wherein the adaptive dispensing parameters are responsive to a $\Delta E$ or corresponding residual efficacy value of the consumables and cosmetic substance being dispensed and may further be responsive to the consumer's input related to the $\Delta E$, the corresponding efficacy value, or the corresponding amount of efficacy content to be dispensed. In this way, the amount of efficacy content in the dispensed consumables and cosmetic substance can be optimized or maintained, according to, but not limited to: a target amount based on the consumer's input regarding his needs or preference; a target amount established by the provider of the consumables and cosmetic substance, such as the transformer; a target amount established by a dispenser of the consumables and cosmetic substance, such as a service provider; or a target amount equal to a predetermined amount of efficacy content recommended by the labeling or product information provided with the consumables and cosmetic substance. In this way, individual A1 is able to achieve the highest corresponding health index at any given time from To, for example his birth, to time T5, for example his expiration or death.

As demonstrated by this example, individual $A_1$'s ultimate consumption and use of nutritional substances and consumables and cosmetic substances has benefited from adaptively determined recommendations responsive to: input from individual $A_1$ regarding his genetic code "$a_1$"; input from individual $A_1$ regarding particular health indices of interest; input regarding the actual residual nutritional and efficacy values of nutritional substances and consumables and cosmetic substances individual $A_1$ has already consumed or used; and $\Delta N$ and $\Delta E$ information for nutritional substances and consumables and cosmetic substances currently being considered for conditioning, consumption, dispensing, or use by individual $A_1$. In this way, individual $A_1$ has optimized the particular health indices and achieved the highest corresponding health index at any given time from $T_0$, for example his birth, to time $T_5$, for example his expiration.

In a further example, individual $A_2$ has a unique genetic code "$a_2$", but has the same genetic profile "A" as individual $A_1$, and accordingly has an initial particular health index value of $H_2$ corresponding to the particular health index value at $T_0$. However, individual $A_2$ does not utilize the $\Delta H$ database. Accordingly, individual $A_2$ is unable to obtain adaptively determined recommendations regarding nutritional and efficacy values needed to optimize the particular health index for individuals with his genetic profile "A". Therefore, he is not able to achieve the highest corresponding health index at any given time from $T_0$, for example his birth, to time $T_2$, for example his expiration.

It is clear from FIG. 1 that individual $A_1$'s utilization of the $\Delta H$ database, along with input regarding his genetic code "$a_1$"; input regarding particular health indices of interest; input regarding the actual residual nutritional and efficacy values of nutritional substances and consumables and cosmetic substances already consumed or used; and $\Delta N$ and $\Delta E$ information for nutritional substances and consumables and cosmetic substances he was currently considering for conditioning, consumption, dispensing, or use, enabled him to achieve a higher corresponding health index at any given time from $T_0$ to $T_5$, than individual $A_2$, who shares the same genetic profile "A" and initial health index value of $H_2$, but does not utilize the $\Delta H$ database. It is also clear that individual $A_1$'s expiration occurs at a later time $T_5$ than individual $A_2$'s expiration at $T_2$.

In an example, individual $B_1$ utilizes information regarding his genetic code "$b_1$" to identify a corresponding genetic profile in the $\Delta H$ database, wherein the corresponding genetic profile "B" is referenced to information regarding nutritional values of nutritional substances and efficacy values of consumables and cosmetic substances, and combinations thereof, required to optimize particular health indices for individuals with genetic profile "B". Input from individual $B_1$ may also include one or more particular health indices of interest, and may further include information regarding the actual residual nutritional and efficacy values of nutritional substances and consumables and cosmetic substances already consumed or used individual $B_1$, wherein such information may have been acquired through his use of the information systems described in detail in copending U.S. patent application Ser. Nos. 13/771,004, 13/888,353, 13/948,004, 13/948,078, 13/948,083, and 14/044,851, the teaching and descriptions of all of which are incorpated herein by reference in their entirety. Responsive to the input from individual $B_1$, the $\Delta H$ database adaptively determines and provide recommendations regarding current needs for consumption or use of nutritional substances and consumables and cosmetic substances so as to optimize corresponding health indices. The adaptive nature of such recommendations takes into account deficient, proper, or excesses levels of particular nutritional values and efficacy values. For example, the input regarding the actual residual nutritional and efficacy values of nutritional substances and consumables and cosmetic substances already consumed or used by individual $B_1$ may compared to, or otherwise evaluated against, the $\Delta H$ database for genetic profile "B", in order to determine currently needed levels of corresponding nutritional and efficacy values. Using the adaptively determined recommendations from the $\Delta H$ database regarding needed nutritional and efficacy values, individual $B_1$ can further utilize the information systems described fully and in detail in copending U.S. patent application Ser. Nos. 13/771, 004, 13/888,353, 13/948,004, 13/948,078, 13/948,083, and 14/044,851 to accomplish conditioning, dispensing, consumption, and use of nutritional substances and consumables and cosmetic substances to assure the consumption and use of required residual nutritional and efficacy values. In this way, individual $B_1$ is able to achieve the highest corresponding health index at any given time from $T_0$, for example his birth, to time $T_4$, for example his expiration.

As demonstrated by this example, individual $B_1$'s ultimate consumption and use of nutritional substances and consumables and cosmetic substances has benefited from adaptively determined recommendations responsive to: input from individual $B_1$ regarding his genetic code "$b_1$"; input from individual $B_1$ regarding particular health indices of interest; input regarding the actual residual nutritional and efficacy values of nutritional substances and consumables and cosmetic substances individual $B_1$ has already consumed or used; and $\Delta N$ and $\Delta E$ information for nutritional substances and consumables and cosmetic substances currently being considered for conditioning, consumption, dispensing, or use by individual $B_1$. In this way, individual $B_1$ has optimized the particular health indices and achieved the highest corresponding health index at any given time from $T_0$, for example his birth, to time $T_4$, for example his expiration.

In a further example, individual $B_2$ has a unique genetic code "$b_2$", but has the same genetic profile "B" as individual $B_1$, and accordingly has an initial particular health index value of $H_1$ corresponding to the particular health index value at $T_0$. However, individual $B_2$ does not begin to utilize the $\Delta H$ database until $T_1$. Accordingly, individual $B_2$ is unable to obtain adaptively determined recommendations regarding nutritional and efficacy values needed to optimize the particular health index for individuals with his genetic profile "B". Therefore, he is not able to achieve the highest corresponding health index at any given time from $T_0$, for example his birth, to time $T_1$ when he begins to utilize the $\Delta H$ database.

At time $T_1$ individual $B_2$ begins to utilize the information regarding his genetic code "$b_2$" to identify a corresponding genetic profile in the $\Delta H$ database, wherein the corresponding genetic profile "B" is referenced to information regarding nutritional values of nutritional substances and efficacy values of consumables and cosmetic substances, and combinations thereof, required to optimize particular health indices for individuals with genetic profile "B". Input from individual $B_2$ may also include one or more particular health indices of interest, and may further include information regarding the actual residual nutritional and efficacy values of nutritional substances and consumables and cosmetic substances already consumed or used individual $B_2$, wherein such information may have been acquired through his use of the information systems described in copending U.S. patent application Ser. Nos. 13/771,004, 13/888,353, 13/948,004, 13/948,078, 13/948,083, and 14/044,851, the teaching and descriptions of all of which are incorpated herein by reference in their entirety. Responsive to the input from individual $B_2$, the $\Delta H$ database adaptively determines and provide recommendations regarding current needs for consumption or use of nutritional substances and consumables and cosmetic substances so as to optimize corresponding health indices. The adaptive nature of such recommendations takes into account deficient, proper, or excesses levels of particular nutritional values and efficacy values. For example, the input regarding the actual residual nutritional and efficacy values of nutritional substances and consumables and cosmetic substances already consumed or used by individual $B_2$ may compared to, or otherwise evaluated against, the $\Delta H$ database for genetic profile "B", in order to determine currently needed levels of corresponding nutritional and efficacy values. Using the adaptively determined recommendations from the $\Delta H$ database regarding needed nutritional and efficacy values, individual $B_2$ can further utilize the information systems described fully and in detail in copending U.S. patent application Ser. Nos. 13/771,004, 13/888,353, 13/948,004, 13/948,078, 13/948,083, and 14/044,851 to accomplish conditioning, dispensing, consumption, and use of nutritional substances and consumables and cosmetic substances to assure the consumption and use of required residual nutritional and efficacy values. In this way, individual $B_2$ is able to achieve the highest corresponding health index at any given time from $T_1$, when he begins utilizing the adaptively determined recommendations, to time $T_3$, for example his expiration.

It is clear from FIG. 1 that individual $B_1$'s utilization of the $\Delta H$ database, along with input regarding his genetic code "$b_1$"; input regarding a particular health index of interest; input regarding the actual residual nutritional and efficacy values of nutritional substances and consumables and cosmetic substances already consumed or used; and $\Delta N$ and $\Delta E$ information for nutritional substances and consumables and cosmetic substances he was currently considering, enabled him to achieve a higher corresponding health index at any given time from $T_0$ to $T_4$, than individual $B_2$, who shares the same genetic profile "B" and initial health index value of $H_1$, but does not begin to utilize the $\Delta H$ database until $T_1$. While individual $B_1$'s expiration occurs at a later time $T_4$ than individual $B_2$'s expiration at $T_3$, it is clear that individual $B_2$ was able to favorably affect the rate of change, in this case a decline, in the particular health index value by beginning to obtain adaptively determined recommendations regarding required residual nutritional and efficacy values from the $\Delta H$ database.

Figure 2:
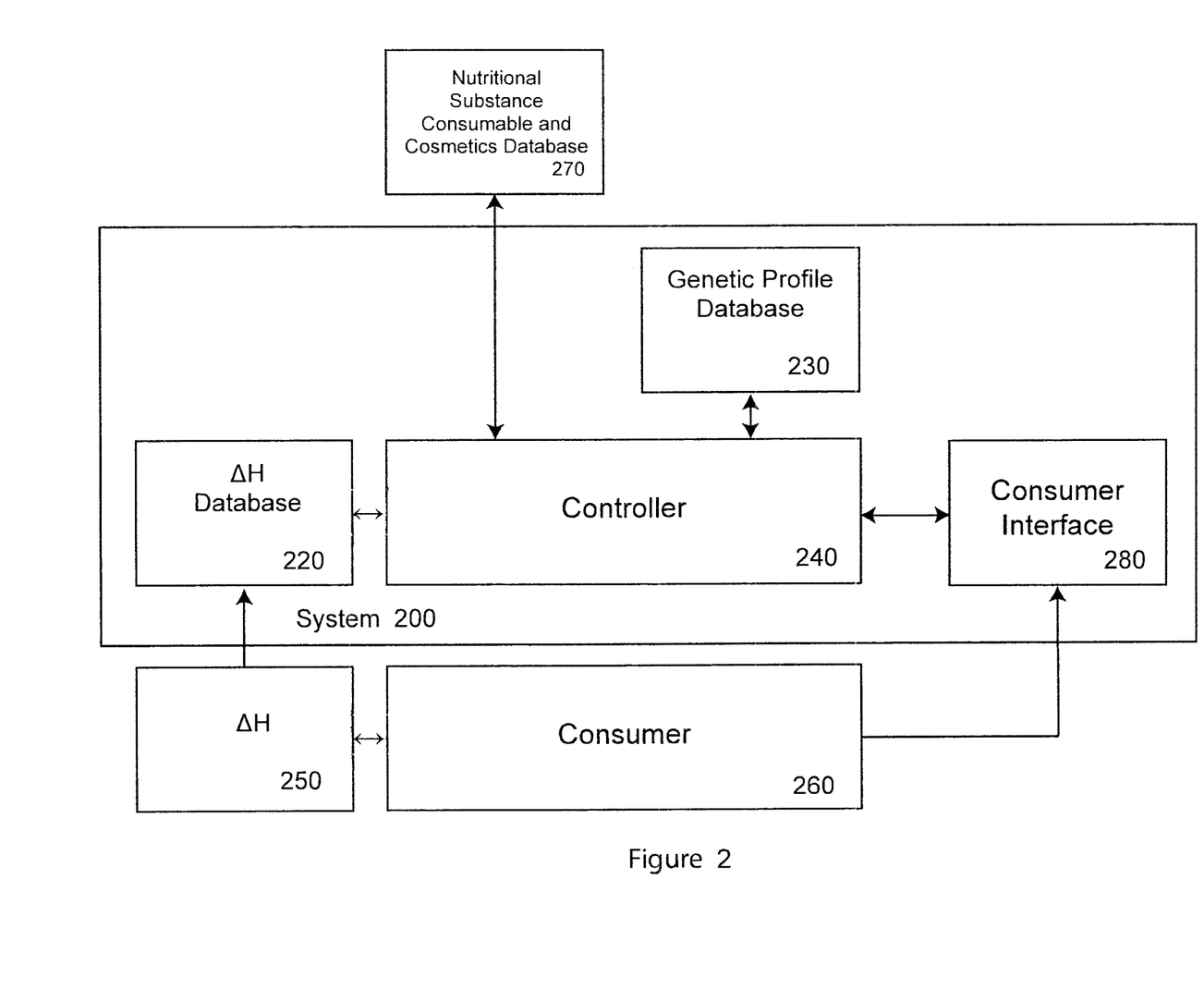
FIG. 2 shows a schematic functional block diagram of one example of a health index system 200 according to one embodiment of the present invention.

FIG. 2 illustrates one embodiment of an exemplary health index system 200 according to some embodiments of the present invention. In this example, health index system 200 includes $\Delta H$ database 220, genetic profile database 230, controller 240 and consumer interface 280. The term "consumer" is used for convenience, however the consumer may be considered to be an individual, patient, health care provider, or any other person or entity that uses or accesses the system. Coupled to the controller 240 may be a nutritional substance/consumables and cosmetics database 270 as described in the co-pending applications cited herein. $\Delta H$ data 250 is read or inputted by consumer 260 into the system 200. $\Delta H$ data 250 represents the various health index values over time of the individual and is tracked and stored over time in the $\Delta H$ database 220.

The genetic profile database 230 may be created by: determining the genetic code of many individuals, and preferably, all individuals; tracking and storing their various health index values over time ($\Delta H$ data 250); referencing the tracked and stored data to its corresponding genetic code; and analyzing the data to identify distinct genetic profiles, wherein each genetic profile includes $\Delta H$ data for individuals with genetic traits that predispose them to experience similar $\Delta H$s when consuming similar nutritional substances and consumables and cosmetic substances.

The data for each genetic profile may be further analyzed to identify information regarding nutritional values of nutritional substances and efficacy values of consumables and cosmetic substances, and combinations thereof, required to optimize various corresponding health indices for individuals with that genetic profile. Such information may comprise the ΔH database 220.

By determining an individual's genetic code, the ΔH database 220 could be used in many ways to improve the health, wellbeing, and/or longevity of the individual. For example, if someone has a large tumor then his doctor can access the ΔH database 220 and determine the best course of action for individuals with the same genetic profile from the generic profile database 230. In this case the ΔH database 220 and genetic profile database 230 may show that individuals sharing this genetic profile lived a long time without the need for the tumor to be removed simply by taking care to not consume particular nutritional values found in specific nutritional substances, for example, specific nutritional values found in milk that accelerate tumors in men but not in women. In contrast a doctor might identify another very small tumor that given the individuals genetic profile, had to be extracted with urgency as regardless of nutritional substance and consumables and cosmetic substances consumed or used, it has a devastating effect if it remained in his body.

Of particular advantage, controller 240 is configured or adapted to process and correlate the genetic profile data and ΔH data. Such processing and correlation may produce an output that is used to determine desired treatment to improve the health, wellbeing, and/or longevity of the individual. Optionally, nutritional substance information and/or consumable and cosmetics data 270 may also be correlated or processed by controller 240 to provide further output that is used to determine desired treatment to improve the health, wellbeing, and/or longevity.

In an alternate embodiment, controller 230 references nutritional substance information and/or consumables and cosmetics information from database 270 to genetic profile database 230 to inform the consumer 260 via consumer interface 280 what impact a particular nutritional substance and/or consumable or cosmetic may have on the consumer given a particular genetic profile.

The health index system 200 can be implemented with discreet devices. Data may be provided in a number of ways, such as by optical reader such as a barcode scanner or camera capable of discerning reference information, by reader such wireless signal reader, reading RFID labels, or near field IDs, by manual input via a keyboard or touch screen, and the like. Controller 240 can be a computer, microcontroller, personal computer, laptop computer, tablet computer, or smartphone. Consumer interface 280 can be a standalone touchpad display panel which allows interaction with the consumer, but is preferably integrated into controller 240.

The utilization of the information systems comprising a AH database, in conjunction with the nutritional substance and consumables and cosmetic substance information systems described in copending U.S. patent application Ser. Nos. 13/771,004, 13/888,353, 13/948,004, 13/948,078, 13/948,083, and 14/044,851, dynamically connects participants and stake holders across the nutritional substance/consumables and cosmetic substance ecosystem in order to improve individuals health, wellbeing, and quality of life. For example, the information module may be implemented as a massive, multidimensional database operated on multiple computing devices across an interconnecting network. Such a database could be hosted by a plurality of nutritional substance creators, preservers, transformers, conditioners, or consumers. In some embodiments, the information module may be maintained and operated by a global entity which operates the system for the benefit of all participants in a nutritional substance supply system. In such an information module, the global entity could be remunerated on a per-transaction basis for receiving nutritional substance information or providing nutritional substance information.

Access to the information module by participants in the supply chain could be at no charge. However, the global entity could receive remuneration for access by non-participants such as research and marketing organizations. Alternatively, participants in the supply chain could pay to advertise to other participants in the supply chain as part of their access to the information in information module.

Unless the context clearly requires otherwise, throughout the description and the claims, the words "comprise," "comprising," and the like are to be construed in an inclusive sense (i.e., to say, in the sense of "including, but not limited to"), as opposed to an exclusive or exhaustive sense. As used herein, the terms "connected," "coupled," or any variant thereof means any connection or coupling, either direct or indirect, between two or more elements. Such a coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the invention is not intended to be exhaustive or to limit the invention to the precise form disclosed above. While specific examples for the invention are described above for illustrative purposes, various equivalent modifications are possible within the scope of the invention, as those skilled in the relevant art will recognize While processes or blocks are presented in a given order in this application, alternative implementations may perform routines having steps performed in a different order, or employ systems having blocks in a different order. Some processes or blocks may be deleted, moved, added, subdivided, combined, and/or modified to provide alternative or sub-combinations. Also, while processes or blocks are at times shown as being performed in series, these processes or blocks may instead be performed or implemented in parallel, or may be performed at different times. Further any specific numbers noted herein are only examples. It is understood that alternative implementations may employ differing values or ranges.

The various illustrations and teachings provided herein can also be applied to systems other than the system described above. The elements and acts of the various examples described above can be combined to provide further implementations of the invention.

Any patents and applications and other references noted above, including any that may be listed in accompanying filing papers, are incorporated herein by reference. Aspects of the invention can be modified, if necessary, to employ the systems, functions, and concepts included in such references to provide further implementations of the invention.

These and other changes can be made to the invention in light of the above Detailed Description. While the above description describes certain examples of the invention, and describes the best mode contemplated, no matter how detailed the above appears in text, the invention can be practiced in many ways. Details of the system may vary considerably in its specific implementation, while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

While certain aspects of the invention are presented below in certain claim forms, the applicant contemplates the various aspects of the invention in any number of claim forms. For example, while only one aspect of the invention is recited as a means-plus-function claim under 35 U.S.C. § 112, sixth paragraph, other aspects may likewise be embodied as a means-plus-function claim, or in other forms, such as being embodied in a computer-readable medium. Any claims intended to be treated under 35 U.S.C. § 112, ¶6 will begin with the words "means for." Accordingly, the applicant reserves the right to add additional claims after filing the application to pursue such additional claim forms for other aspects of the invention.

I claim:

1. A system for tracking and/or optimizing one or more health indices associated with an individual, the system comprising:
   a computer system having memory containing machine executable code;
   a genetic profile database that collects genetic code data for individuals and identifies corresponding genetic profiles based on the genetic code data;
   a $\Delta H$ database that contains $\Delta H$ data associated with each of the genetic profiles, the $\Delta H$ data comprising changes in one or more health indices associated with an individuals' health over time;
   the $\Delta H$ database further contains information regarding nutritional values of nutritional substances, and at least one $\Delta N$ value, wherein $\Delta N$ is a change in the nutritional value of the nutritional substances over time;
   a consumer interface configured to receive information regarding actual residual nutritional values of nutritional substances already consumed by an individual; and
   a controller, coupled to the memory, and comprising one or more processors, the one or more processors configured to execute the machine executable code to:
   correlate, by the controller, the genetic code data and $\Delta H$ data and $\Delta N$ value of the nutritional substances,
   determine, by the controller, needed levels of nutritional values based on the actual residual nutritional values of the already consumed nutritional substances, the correlated genetic code data, the $\Delta H$ data and the $\Delta N$ value,
   output the correlated $\Delta H$ data to an individual wherein an individual tracks or adaptively manages external factors the individual experiences so as to optimize the $\Delta H$ based on the individual's particular genetic profile and the $\Delta N$ value of the nutritional substances the individual may consume as determined by the controller, and
   execute, by the controller, conditioning of nutritional substances to achieve the needed levels of nutritional values determined by the controller.

2. The system of claim 1 wherein the one or more health indices are comprised of quantitative or qualitative values or scores associated with quality of life, disease state, disease resistance, vital signs, blood chemistry, strength, endurance, metal elasticity, or other factors associated with an individuals' health or wellbeing.

3. The system of claim 1 wherein the $\Delta H$ database further contains information regarding efficacy values of consumables and cosmetic substances, and combinations thereof, and such information is correlated to one or more of the health indices for a given genetic profile.

4. The system of claim 1 wherein the $\Delta H$ database further contains $\Delta N$ is the actual residual nutritional value of the nutritional substance an individual plans to prepare or consume.

5. The system of claim 4 wherein $\Delta N$ is a change in the nutritional value of the nutritional substance and said change comprises any of a maintenance, improvement, or degradation.

6. The system of claim 1 wherein the $\Delta H$ database further contains at least one $\Delta E$ value, wherein $\Delta E$ is the actual residual efficacy value of the consumables or cosmetics substances an individual plans to consume or use, or a change in the efficacy value of the consumables or cosmetics substances over time.

7. The system of claim 1 further comprising a consumer interface configured to receive $\Delta H$ information.

8. The system of claim 7 wherein the consumer interface is further configured to provide $\Delta H$ information.

9. The system of claim 1 wherein said controller comprises a computer.

10. The system of claim 1 wherein said system comprises an internet database running on one or more servers.

11. The system of claim 1 further comprising an additional database containing information regarding nutritional values of nutritional substances and efficacy values of consumables and cosmetic substances, and combinations thereof, and such information is correlated to one or more of the health indices for a given genetic profile.

* * * * *